(12) United States Patent
Liu

(10) Patent No.: US 7,141,371 B2
(45) Date of Patent: Nov. 28, 2006

(54) METHODS FOR DETECTING AND LOCALIZING DNA MUTATIONS BY MICROARRAY

(75) Inventor: Guowen Liu, Eugene, OR (US)

(73) Assignee: State of Oregon Acting by and through the State Board of Higher Education on behalf of the University of Oregon, Eugene, OR (US)

( * ) Notice: Subject to any disclaimer, the term of this patent is extended or adjusted under 35 U.S.C. 154(b) by 553 days.

(21) Appl. No.: 10/236,598

(22) Filed: Sep. 6, 2002

(65) Prior Publication Data

US 2004/0048257 A1    Mar. 11, 2004

(51) Int. Cl.
  C12Q 1/68   (2006.01)
  C12P 19/34  (2006.01)
(52) U.S. Cl. .......................................... 435/6; 435/91.1
(58) Field of Classification Search ................ 435/67.1, 435/174, 283.1, 6, 91.1, 91.2; 422/40, 68.1, 422/82.05
See application file for complete search history.

(56) References Cited

U.S. PATENT DOCUMENTS

| | | | | |
|---|---|---|---|---|
| 4,794,075 | A * | 12/1988 | Ford et al. | 435/6 |
| 5,698,400 | A * | 12/1997 | Cotton et al. | 435/6 |
| 5,723,320 | A * | 3/1998 | Dehlinger | 435/91.1 |
| 5,728,524 | A | 3/1998 | Sibson | |
| 5,750,335 | A * | 5/1998 | Gifford | 435/6 |
| 5,922,535 | A * | 7/1999 | Huo | 435/6 |
| 6,468,742 | B1 | 10/2002 | Nerenberg | |
| 6,713,258 | B1 | 3/2004 | Kilian | |
| 6,783,943 | B1 * | 8/2004 | Christian et al. | 435/6 |
| 6,924,104 | B1 * | 8/2005 | Weissman et al. | 435/6 |
| 2002/0146723 | A1 * | 10/2002 | Krontiris et al. | 435/6 |

| 2005/0032082 | A1 | 2/2005 | Kilian |

FOREIGN PATENT DOCUMENTS

| WO | WO 00/44936 | 8/2000 |
|---|---|---|
| WO | WO 00/50632 | 8/2000 |
| WO | WO 2004/044225 | 5/2004 |

OTHER PUBLICATIONS

Buckley, "Development and Application of Micrarray-Based Comparative Genomic Hybridization: Analysis of Neurofibromatosis Type-2, Schwannomatosis and Related Tumors," Abstract for Doctoral Thesis from Uppsala Univesity, *Comprehensive Summaries of Uppsala Dissertations from the Faculty of Medicine* (Feb. 2005).

(Continued)

*Primary Examiner*—Kenneth R. Horlick
(74) *Attorney, Agent, or Firm*—Klarquist Sparkman LLP

(57) ABSTRACT

This disclosure provides methods for detecting and localizing DNA mutations by DNA microarray. In various embodiments, the described methods include use of restriction endonuclease(s) and/or mismatch-recognition nuclease(s) to detect and/or localize mutations. In one representative method, reference and target DNA are digested using one or more restriction endonucleases, resultant DNA strands are labeled (e.g., using a DNA polymerase), and the labeled mixture of DNAs is hybridized to a microarry. In another representative method, reference and target DNA are denatured and annealed to form a mixture containing heteroduplex DNA, one or more mismatch-recognition nuclease(s) are used to nick or cleave at least a portion of the heteroduplex DNA, resultant DNA strands are labeled (e.g., using a DNA polymerase) and the labeled mixture of DNAs is hybridized to a microarray.

10 Claims, 4 Drawing Sheets

OTHER PUBLICATIONS

Chee et al., "Accessing Genetic Information with High-Density DNA Arrays," *Science*, 274(5287):610-614 (Oct. 1996).

Gotoh and Oishi, "Screening of Gene-Associated Polymorphisms by Use of In-Gel Competitive Reassociation and EST (cDNA) Array Hybridization," *Genome Research*, 13:492-495 (2003).

Hacia, "Resequencing and mutational analysis using oligonucleotide microarrays," *Nature Genetics Supplement*, 21:42-47 (Jan. 1999).

Liu et al., "SNP selection for a microarray based high-throughout genotyping assay," Abstact for a poster presented at Jul. 31-Aug. 4, 2004, meeting— 12th International Conference on Intelligent Systems for Molecular Biology (accessible on-line at http://www.iscb.org/ismb2004/posters/guoying_liuATaffymetrix.com_463.html).

Lucito et al., "Representational Oligonucleotide Microarray Analysis: A High-Resolution Method to Detect Genome Copy Number Variation," *Genome Research*, 13:2291-2305 (2003).

Martin et al., "A rapid method to map mutations in *Drosophila*," *Genome Biology*, 2(9):1-12 (Aug. 2001).

Wang et al., "Large-Scale Identification, Mapping and Genotyping of Single-Nucleotide Polymorphisms in the Human Genome," *Science*, 280:1077-1082 (May 1988).

Jaccoud et al., "Diversity Arrays: a solid state technology for sequence information independent genotyping," *Nucleic Acids Research*, 29(4):1-7 (2001).

* cited by examiner

Figure 3A
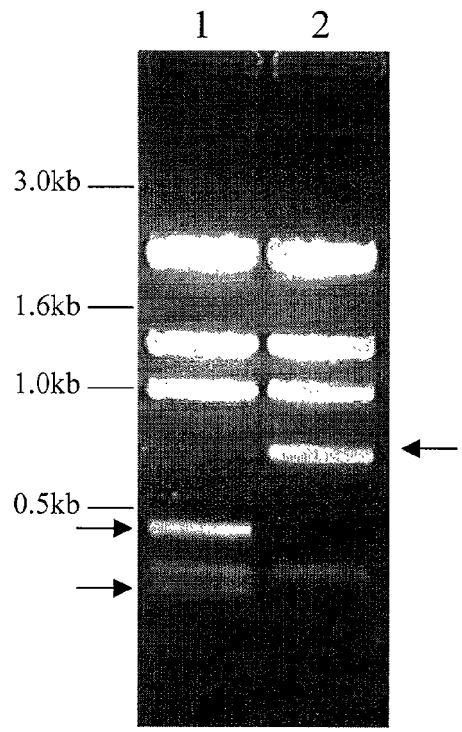
Figure 3B
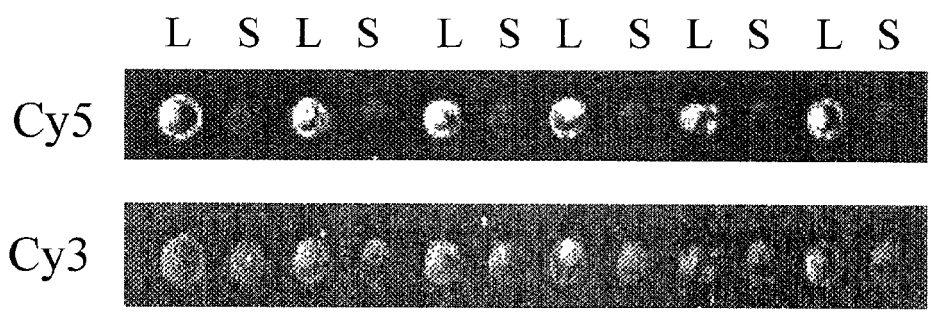
Figure 3

METHODS FOR DETECTING AND LOCALIZING DNA MUTATIONS BY MICROARRAY

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

Detection and identification of simple nucleotide mutations and/or polymorphisms among individuals are very important in many biological fields, ranging from biomedical research in hereditary diseases to ecology and evolutionary biology. Identification of the location of mutations involved in heritable diseases can provide clues for the diagnosis, prognosis and therapeutic treatment of such diseases. However, it is very difficult to localize most of the mutations into very small region (several kilo-base pairs) or a single gene at a genomic level.

Sequencing of the genome of different individuals is the most straightforward method for mutation detection, but it is expensive and time-consuming. Some methods have been developed to detect mutations without direct sequencing. Linkage and association mapping use polymorphic markers to approximate the chromosomal location of the mutations. This method is very efficient to localize a mutation into a quite large genomic region (several hundreds kilo-base pairs), but very slow to further localize it into a single gene or a small region (several kilo-base pairs). Restriction fragment length polymorphism (RFLP) is good for mutation detection and sequence comparison but can not efficiently define the location of a mutation either if whole genomic DNA is used as the starting material.

Most of the currently developed methods or techniques are suitable for testing mutations in a small region or a handful of genes, but are not good (if not impossible) for localizing mutations or polymorphisms at a genomic level. For example, in polynucleotide microarray hybridization methods (e.g. U.S. Pat. No. 5,837,832 (Chee et al.), and U.S. Pat. No. 6,376,191 (Yu et al.)) mutations in every single base position are detected by a set of four primers. To fully detect a 10 kb region, these methods will need about 10,000 sets of primers to be spotted on a microarray slide. Single stranded conformational polymorphism (SSCP) and denaturing gradient gel electrophoresis (DGGE) (Orita et al (1989) PNAS 86:2766; Myers et al (1985) *N. A. R.* 13:3131; White et al (1992) *Genomics* 5:301; Mills et al (1994) *Biochem.* 33:1797) methods are based on the observations that DNA sequence variations can cause DNA electrophoretic mobility changes. These two methods only work with short DNA molecules and can not screen many genes simultaneously.

The two methods I present in this invention have great potential to detect and localize DNA mutations at a genomic level simultaneously and rapidly. The method using restriction endonuclease(s) to detect mutations is termed RE microarray method. The other method using mismatch-recognition endonuclease(s) is named MR microarray method. The principle of the methods is illustrated in FIG. 1.

BRIEF SUMMARY OF THE INVENTION

Mutation detection is very important for the diagnosis, prognosis and therapeutic treatment of heritable diseases. However, none of the known methods can efficiently detect and define the location of mutations at a genomic level. In this invention, two methods are provided for such a purpose. The RE mutation detection microarray method used restriction endonuclease to detect mutations and the MR microarray method used mismatch-recognition nuclease to detect mutations. In the RE microarray method, the reference and target DNAs were completely digested with a restriction endonuclease. If a mutation caused the elimination of a restriction site of the endonuclease, the two restriction fragments in the reference DNA flanking the position of the mutation would in the target DNA become one large fragment spanning the position of the mutation. After denaturation and annealing, one single strand from the above two fragments of the reference DNA could anneal with one strand of the above large fragment of the target DNA to form a partially double-stranded DNA and DNA polymerase could then use the short strand of this DNA as a primer and the long strand as a template to label the short strand DNA by incorporating fluorescent nucleotides into newly synthesized DNA. Therefore, by this mechanism only the DNA strands flanking the mutation could be labeled. When hybridized to a microarray slide, the labeled DNA would bind to the spot whose DNA has the same sequence as the labeled DNA. By identification of the sequence of the spot DNA, the mutation would then be localized at or around this DNA sequence region, which can be as small as several kilobases. Similarly, a mutation that created a restriction site of the applied restriction endonuclease can also be detected and localized by this method.

In the MR mutation detection microarray method, reference DNA and target DNA were mixed, fragmented (by a restriction endonuclease), denatured and annealed to form heteroduplex DNA (between a single strand of a reference DNA fragment and a strand of the corresponding target DNA fragment carrying a mutation) as well as homoduplex DNA. The heteroduplex DNA was then specifically recognized and cleaved around the mismatch site into two short fragments by a mismatch-recognition nuclease while its corresponding homoduplex DNA and other homoduplex DNA would not be cleaved and kept full length. After re-denaturation and re-annealing of the nuclease-treated DNA mixture, a single strand of the cleaved short DNA fragments could anneal to a single strand of its corresponding full length DNA fragment to form a partially double-stranded DNA. As described in the RE microarray method, DNA polymerase could then use this partially double-stranded DNA to label the DNA strands flanking the mutation and after hybridization to a DNA microarray the location of the mutation would be identified.

In practice, both methods also used a differently labeled control DNA. The control DNA is the reference DNA alone or the target DNA alone treated in the same way as the mixture of the reference and target DNA as described above but labeled differently from the mixture of reference and target DNA. The differently labeled control DNA would then be combined with the labeled mixture DNA and hybridized to a microarray slide. The mutations would be detected and localized by identifying the sequence of each DNA whose microarray spot had a higher ratio of the label signal from the mixture DNA to the label signal from the control DNA. Such a control could reduce the effect of non-specific cutting or digestion by the nuclease and varied DNA amounts of different microarray spots, etc.

To prove the practicability of the methods, mutations in plasmids were detected and localized. A wild type plasmid was divided into two regions, L and R, and two DNA molecules separately from the two regions were used to spot onto slides to make mini microarrays. Three mutant plasmids (target DNAs) were compared with the wild type parental plasmid (reference DNA) by the methods. One of the mutant plasmids had a mutation that caused the elimination of an Ase I restriction site and the RE mutation detection microarray method successfully detected and localized the mutation into L region. The other two mutant plasmids each had a single nucleotide mutation and the MR mutation detection microarray method correctly detected and identified the location of the mutations. These experimental results indicate that the methods are practical and successful in mutation detection.

BRIEF DESCRIPTION OF THE DRAWINGS

FIG. 3a shows the difference of restriction patterns between a wild type plasmid and a mutant plasmid where an Ase I site is missing.

FIG. 3b shows that the mutation that caused the missing of an Ase I site in a mutant plasmid can be detected and correctly localized by the RE microarray method.

Figure 1:
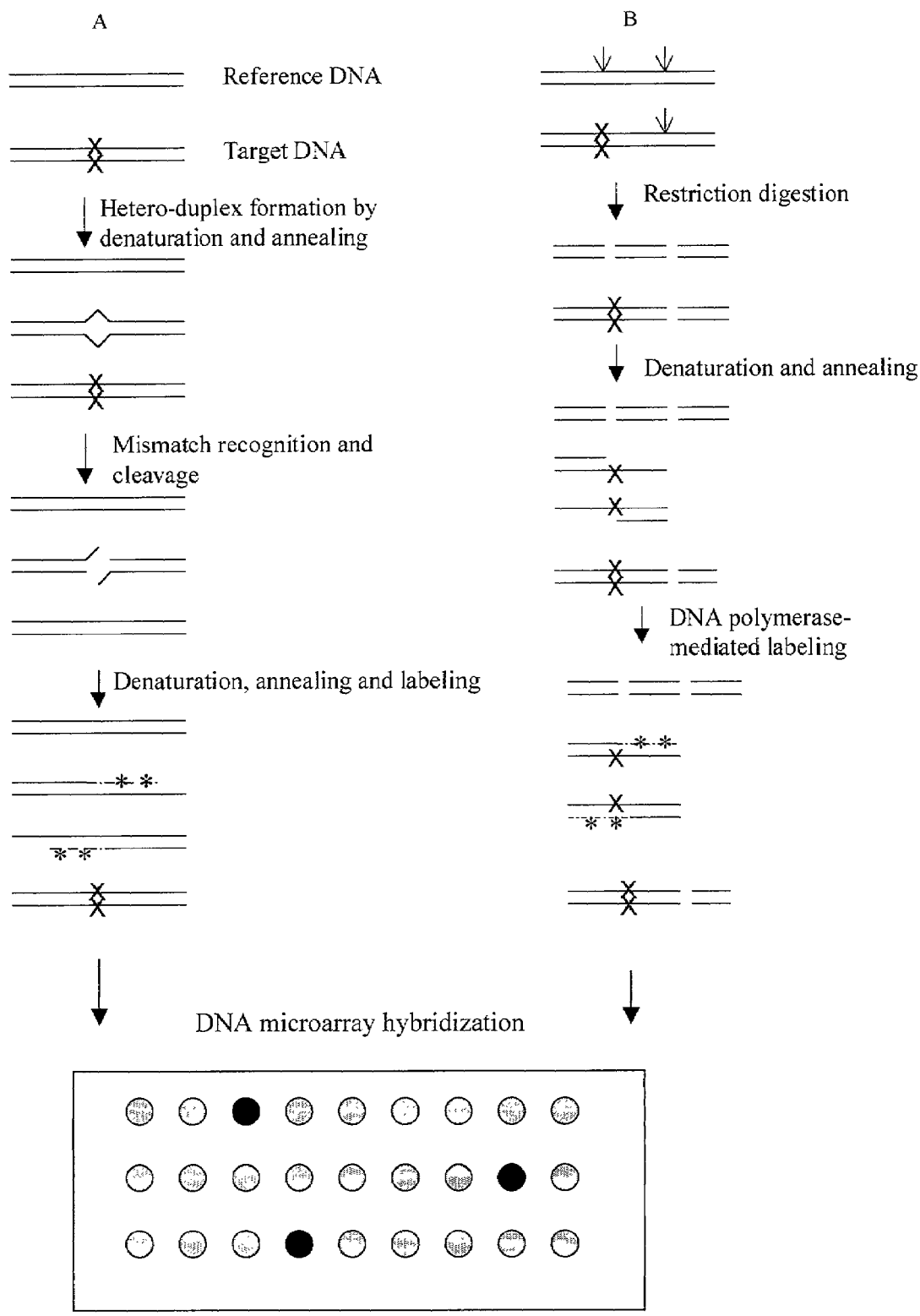
FIG. 1 depicts the principal of the method.

DETAILED DESCRIPTION OF THE INVENTION.

Materials used in this invention are listed as follows:

All the restriction endonucleases used were from New England Biolabs Inc. Taq DNA polymerase, its reaction buffer and dNTPs were from Roche Applied Science. QIAquick gel extraction kit was used for isolating DNA fragments from agarose gel and QIAquick PCR purification kit was used to purify DNA fragments from enzymes, nucleotides and salts (from Qiagen GmbH). Cy3 and Cy5-labeled dCTPs were from Amersham Biosciences.

Wild type (reference DNA) and mutant plasmids (target DNAs) used in this work were from Tom H. Stevens lab in the University of Oregon. pKH28 was constructed by inserting a 795 bp fragment carrying a wild type VMA21 gene in between the Sac I and Kpn I sites of pRS 316. pLG119 has a T to A substitution at 2106 bp. pLG120 has an A to C substitution at 2109 bp and pLG125 has an adjacent two nucleotides substitution (AT to GC) at 2126 bp and 2127 bp, which happens to eliminate an Ase I cutting site (ATTAAT) by changing the first AT to GC. In this work pKH28 is called wild type plasmid DNA or reference DNA. pLG119, 120 and 125 are called mutant plasmid DNA or target DNA.

The DNA microarray slides were made according to the protocols published at web site http://www.microarrays.org, which is maintained by Stanford University. Plasmid pKH28 and its derivatives pLG119, 120 and 125 all have two Sca I restriction sites (FIG. 2) In this invention, the two Sca I sites were used to separate the plasmid into two regions (L and S) (see FIG. 2) and the novel methods were tested to see if it could localize the mutations into a correct region. Therefore, a very simple DNA microarray was made, which only contains two different DNA molecules: a large Sca I fragment molecule (L region DNA) and a small Sca I fragment molecule (S region DNA). These two DNA fragments were isolated from plasmid pKH28 DNA after digestion with Sca I, separation on agarose gel and purification. The two DNAs were spotted onto glass slides in a tandem repeat order as L, S for six times. Therefore there are six spots for each DNA per microarray slide.

Cel I nuclease, a mismatch-recognition enzyme, was prepared from celery according to a published method (Yang et al (2000) *Biochem.* 39: 3533)) with some modifications and less steps of purification. Briefly, 10 kg of fresh celery stalks was homogenized with a juicer and the juice was collected and adjusted to the composition of buffer A (100 mM Tris-HCL, pH7.7, 0.5M KCL and 100 µM PMSF). The suspension was centrifuged at 8000 g for 30 min and the supernatant was collected. 10 ml of Concanavalin A-sepharose (from Sigma) resin was added into the cleared supernatant and gently shaking for overnight at 4° C. The resin was then pelleted and washed twice with buffer A by two cycles of centrifugation (at 3000 g for 30 min) and resuspension. Cel I was then eluted from the resin with 80 ml of buffer A containing 0.3 M α-methyl-mannoside by incubation at 4° C. for four hours with gentle shaking. After centrifugation, the Cel I nuclease solution (supernatant) was collected, aliquot and stored at −20° C. When needed, an aliquot of the enzyme would be thawed and used. For the cleavage of mismatched double-stranded DNA, the best condition for a reaction of 2 µg DNA in a 30 µl final volume in 1× Cel I reaction buffer (20 mM Tris-HCL pH7.4, 25 mM KCL, 10 mM MgCl2) was 1 µl of this Cel I preparation and 30 min incubation at 37° C.

The following examples are intended to illustrate the present invention and should in no way be construed as limiting the invention.

EXAMPLE 1

Detection and Localization of DNA Mutations by the RE Mutation Detection Microarray Method.

Restriction fragment length polymorphism (RFLP) is one of the most popularly used methods for mutation detection and sequence comparison. However, it can not define the location of the mutation. In this experiment, a microarray method is developed for rapid detection and localization of DNA mutations.

Figure 2:
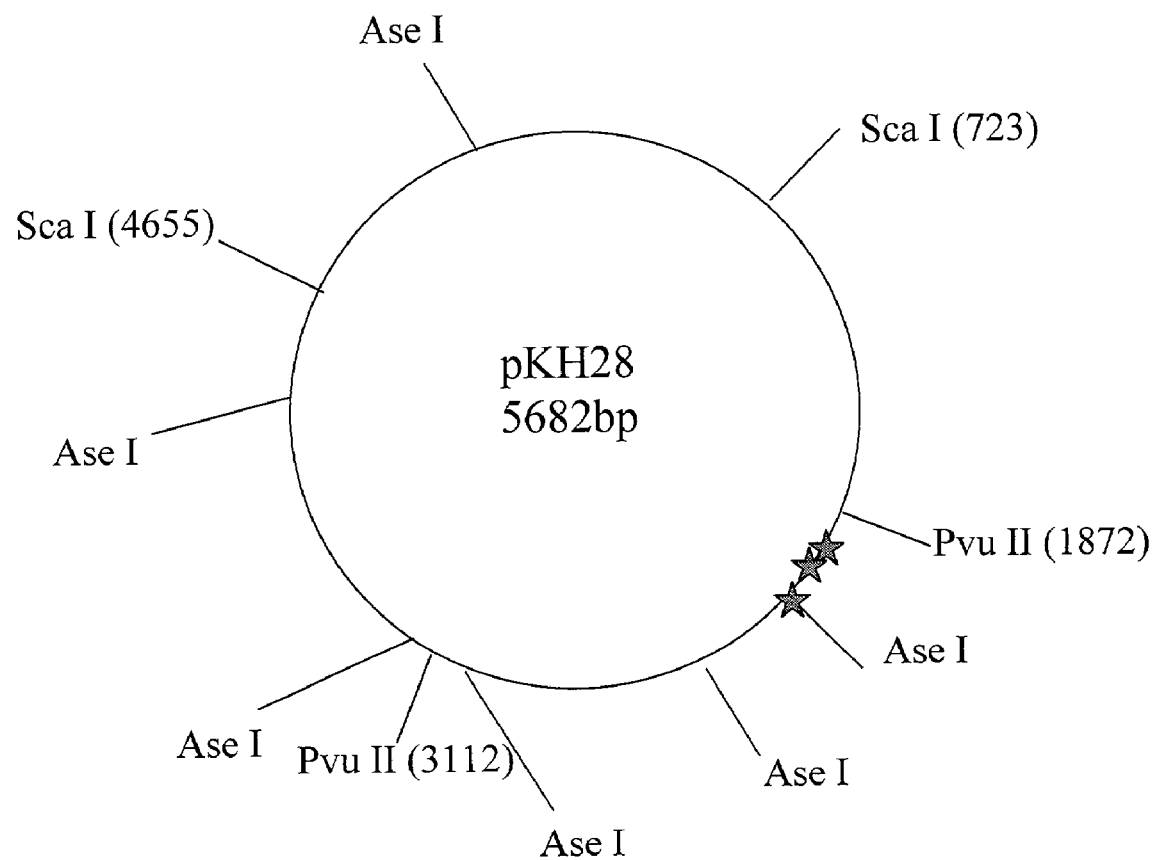
FIG. 2 shows the map of the parental plasmid DNA. The locations of the mutations in target plasmid are also indicated.

A mutation in a mutant plasmid pLG125 caused the missing of an Ase I site, which is present in the wild type plasmid pKH28 (see Materials and FIG. 2).

One microgram (µg) of pLG125 and pKH28 were double digested with Pvu II and Ase I in NEB buffer 2 plus BSA, purified with QIAquick PCR purification kit and resuspended in 30 microliter (µl) of EB buffer (10 mM Tris-HCL, pH8.0). 5 µl of the above digested pKH28 DNA was mixed with 5 µl of the above pLG125 DNA to give a heteromixture DNA. 10 µl of the above digested pKH28 was also taken and called a control DNA. To label the DNA, the following chemicals were added to each of the mixtures: 2 µl of Taq DNA polymerase buffer (with 2.0 mM MgSO4), 5 µl of dATP, dTTP and dGTP mixture each at a concentration of 2 mM, 1 µl of 2 mM dCTP, 1 µl of 1 mM Cy5-dCTP (for hetero-mixture DNA) or Cy3-dCTP (for the control DNA), and 1 μl of Taq DNA polymerase (1 unit). A PCR machine was then used to complete the labeling reaction by a program that the first step is 95° C. 2 min to denature double-stranded DNA, then run 15 cycles of 95° C. 1 min and 72° C. 2 min, followed by a step of 72° C. 15 min and finally stop the reaction by quickly cooling to 4° C. The labeled reaction mixtures were combined, purified by QIAquick PCR purification kit and eluted with 30 μl of EB buffer (10 mM Tris-HCl, pH8.0). 10.5 μl was taken out to mix with 3 μl of 20×SSC, 1.1 μl 20 mg/ml polyA and 0.42 μl of 10% SDS. After heated at 100° C. for 2 min and briefly centrifuged the mixture was then loaded onto a microarray slide for hybridization at 65° C. for 4–16 hours. After scanning of the microarray slides, it was found that in the same microarray slide the Cy5/Cy3 ratio of any spot of the L region DNA was about 5 to 9 times higher than that of any spot of the S region DNA (see FIG. 3). This clearly localizes the mutation into L region in pLG125 plasmid, which is correct, indicating this method is feasible in mutation detection and localization.

EXAMPLE 2

Detection and Localization of DNA Mutations by the MR Mutation Detection Microarray Method.

This experiment composes of four major steps: formation of heteroduplex and homoduplex DNA; treatment of the duplexes with a mismatch-recognition endonuclease to cleave the heteroduplexes at the mismatch site; labeling the cleaved DNA by DNA polymerase-mediated incorporation of modified nucleotides; and hybridizing the labeled DNA to DNA microarray.

There are a few mismatch-recognition endonucleases such as SP nuclease and Mung Ben nuclease. Here, Cel I nuclease was chosen to use because of its high specificity of cleavage at all single nucleotide substitutions (Oleykowski et al (1998) *Nucleic Acids Research* 26: 4597).

To detect and localize a mutation in plasmid pLG119, both pLG119 and wild-type plasmid pKH28 were digested with Sca I and then purified with QIAquick PCR purification kit. One microgram of this Sca I-digested pLG119 (pLG119/Sca I) was mixed with one microgram of the Sca I-digested pKH28 (pKH28/Sca I) in 30 microliter of 2×Cel I reaction buffer. As a control, two micrograms of the pKH28/Sca I were also resuspended in 30 μl of 2×Cel I reaction buffer and would experience exactly the same treatment as the wild type and mutant DNA mixture. The mixtures were then denatured at 95° C. for 5 min, cooled to 85° C. quickly and then slowly cooled down to 30° C. at a speed of 3° C. per hour. This denaturation and annealing step was processed in a PCR machine. In the pKH28/Sca I and pLG119/Sca I mixture, both homoduplexes and heteroduplexes would form randomly. The pKH28/Sca I control would be mainly homoduplexes.

Figure 4:
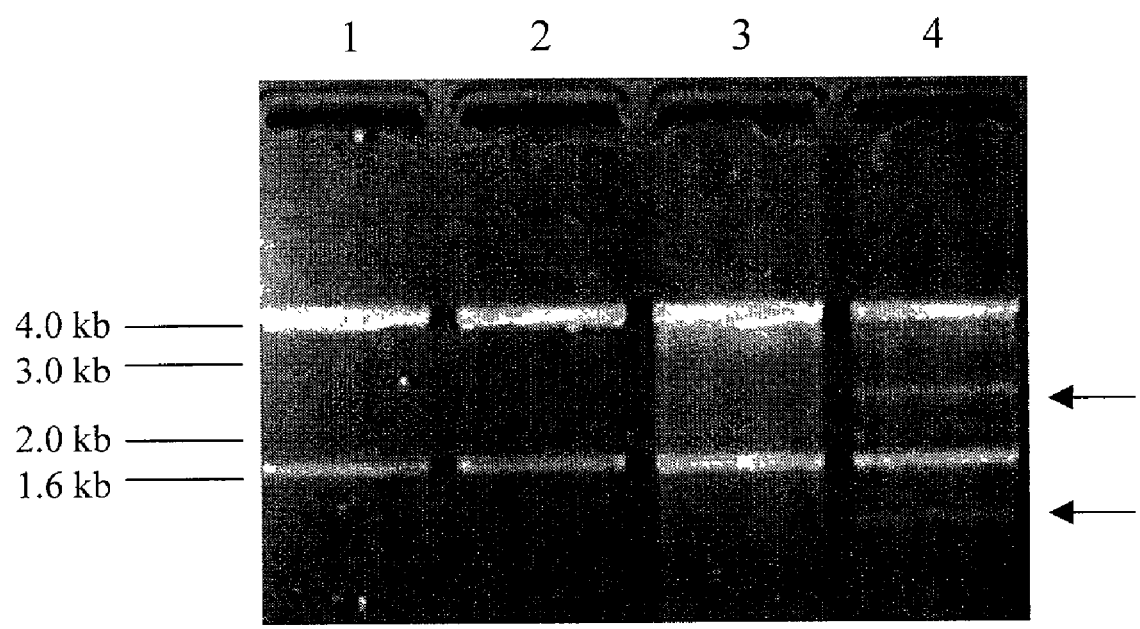
FIG. 4 shows the cleavage of a heteroduplex DNA by Cel I nuclease.

After the formation of heteroduplexes, 28 μl of sterile distilled water was added to each of the above DNA mixtures to get a total of 58 μl. To cleave heteroduplex DNA, 1 μl of Cel I preparation was added into 29 μl of each of the mixtures and incubated at 37° C. for 30 min. After immediate purification with a QIAquick PCR purification kit, each of the Cel I-treated DNA mixtures was resuspended in 30 μl of EB buffer (10 mM Tris-HCL, pH8.0). 6 μl of each was taken and loaded onto 1.0% agarose for gel electrophoresis. It was shown that Cel I could cleave heteroduplexes and produce two new smaller fragments (FIG. 4). It was also shown that Cel I had quite strong non-specific cutting because there was some smear on both of the lanes loaded with Cel I-treated DNA. This is consistent with a former publication (Sokurenko et al (2001) Nucleic Acids Research 29: e111), where Cel I caused significant non-specific digestion of duplex DNA.

To detect the cleaved DNA, Taq DNA polymerase was used to add fluorescent Cy3 or Cy5-dCTP onto it. For this purpose, 10 μl of each of the above purified Cel I-treated DNA was mixed with 2 μl of Taq DNA polymerase buffer (with 2.0 mM MgSO4), 5 μl of dATP, dTTP and dGTP mixture each at a concentration of 2 mM, 1 μl of 2 mM dCTP, 1 μof 1 mM Cy5-dCTP (for DNA from the mixture of pKH28/Sca I and pLG 119/Sca I) or Cy3-dCTP (for the control DNA), and 1 μl of Taq DNA polymerase (1 unit). A PCR machine was then used to complete the labeling reaction by a program that the first step is 95° C. 2 min to denature double-stranded DNA, then run 15 cycles of 95° C. 1 min and 72° C. 2 min, followed by a step of 72° C. 15 min and finally stop the reaction by quickly cooling to 4° C. The labeled reaction mixtures were combined, purified by QIAquick PCR purification kit and eluted with 30 μl of EB buffer (10 mM Tris-HCl, pH8.0). 10.5 μl was taken out to mix with 3 μl of 20×SSC, 1.1 μl 20 mg/ml polyA and 0.42 μl of 10% SDS. After heated at 100 ° C. for 2 min and briefly centrifuged the mixture was then loaded onto a microarray slide for hybridization at 65° C. for 4–16 hours.

The localization of the mutation can be achieved by comparing the ratios (Cy5/Cy3) of different DNA spots. With more than six repeats of the above experiments and each experiment with 6 repeated spots for each DNA fragment, it was found that in the same microarray slide the Cy5/Cy3 ratio of any spot of the L region DNA was 0.4–0.7 times higher than that of any spot of the S region DNA. This predicts that the mutation carried by plasmid pLG119 was located on the large Sca I fragment, which is correct according to the known fact that the mutation is there. This indicates that though there is quite strong non-specific cutting by Cel I nuclease, this method was still able to detect and localize DNA mutation.

Plasmid pLG120, which has an A to C substitution, was also used to test this method. A positive result very similar to that from pLG119 was obtained again. This further proved the practicability of this method and indicated the result of this method is repeatable and reliable. This metbod should work on genomic microarray in a similar way and then DNA mutations or polymorphisms in individual genomes would be able to be detected and localized rapidly.

What I claim as my invention is:

1. A method for detecting and localizing one or more DNA mutations in a target DNA as compared to a reference DNA, the method comprising:
  a) using a restriction endonuclease(s) to digest a mixture of the reference and target DNA or to digest the reference and target DNA separately and then mix, wherein the restriction endonuclease(s) digest the reference and target DNA into different DNA fragments around the position of any mutation that causes the elimination or creation of a restriction site of the endonuclease(s): two short restriction fragments flanking the position of the mutation and a large fragment spanning the position of the mutation;
  b) labeling DNA strands flanking mutations by one or more cycles of denaturation, annealing and labeling with a DNA polymerase(s), wherein denaturation and annealing allow one single strand from the short fragments flanking a mutation to anneal with one strand of the large fragment spanning the mutation to form such a partially double-stranded DNA that a DNA polymerase(s) uses the short strand of this DNA as a primer and the long strand as a template to label the short strand DNA by incorporating modified nucleotides into newly synthesized DNA;

c) hybridizing a combination of the above labeled DNA and a labeled control DNA to at least one DNA microarray, which microarray comprises spots comprising at least one DNA probe, at least some of the spots comprising a DNA probe from the target DNA or the reference DNA, or both; and d) identifying the sequence of at least one DNA from a spot that has significantly higher ratio of the label signal from the mixture of reference and target DNA to the label signal from the control DNA than at least one other spot on the microarray, wherein a labeled control DNA is (1) the reference DNA alone or (2) the target DNA alone treated in the same way as the mixture of reference and target DNA in steps a) and b), but labeled differently from the mixture of reference and target DNA, thereby detecting and localizing DNA mutations.

2. The method of claim 1, wherein the restriction endonuclease(s) is a restriction endonuclease or an agent that binds to specific DNA sequence and cleaves or nicks DNA at or near the specific sequence, or a mixture of different restriction endonucleases and/or the above described agents.

3. The method of claim 1, wherein the DNA polymerase(s) is a DNA polymerase or a mixture of two or more different DNA polymerases.

4. The method of claim 1, wherein the DNA microarray is a genomic DNA array.

5. A method for detecting and localizing DNA mutations in a target DNA as compared to a reference DNA, the method comprising:

a) denaturing and annealing of a mixture of the reference and target DNA to form heteroduplex DNA, its corresponding homoduplex DNA and other homoduplex DNA, wherein the mixture of the reference and target DNA is a mixture of fragmented reference and target DNA, obtained by fragmenting the mixture of the reference and target DNA with a restriction endonuclease(s) or fragmenting the reference and target DNA separately and then mixing them together;

b) using a mismatch-recognition nuclease(s) to nick or cleave at least some of the heteroduplex DNA, wherein the mismatch-recognition nuclease(s) will nick or cleave the heteroduplex DNA at or around the position of any mutation that causes a mismatch detectable by the nuclease(s), but will not specifically nick or cleave its corresponding homoduplex DNA and other homoduplex DNA;

c) labeling DNA strands flanking mutations by one or more cycles of denaturation, annealing and labeling with a DNA polymerase(s), wherein denaturation and annealing will allow one short single strand from the nicked or cleaved heteroduplex DNA to anneal with one long strand from its corresponding homoduplex DNA or one intact strand from the nicked heteroduplex DNA to form such a partially double-stranded DNA that a DNA polymerase(s) uses the short strand of this DNA as a primer and the long strand as a template to label the short strand DNA by incorporating modified nucleotides into newly synthesized DNA;

d) hybridizing a combination of the above labeled DNA and a labeled control DNA to at least one microarray, which microarray comprises spots comprising at least one DNA probe, at least some of the spots comprising a DNA probe from the target DNA or the reference DNA, or both; and e) identifying the sequence of at least one DNA from a spot that has a significantly higher ratio of the label signal from the mixture of reference and target DNA to the label signal from the control DNA than least one other spot on the microarray, wherein a labeled control DNA is (1) the reference DNA alone or (2) the target DNA alone treated in the same way as the mixture of reference and target DNA in steps a), b) and c) but labeled differently from the mixture of reference and target DNA, thereby detecting and localizing DNA mutations.

6. The method of claim 5, wherein the mismatch-recognition nuclease(s) is a nuclease cleaving or nicking DNA heteroduplexes, or a combination of different nucleases.

7. The method of claim 5, wherein the mismatch-recognition nuclease(s) is a naturally existing nuclease(s), or an artificial enzyme constructed by fusing a mismatch-recognition protein or peptide to a nuclease, or a combination of any of the enzymes.

8. The method of claim 5, wherein the DNA polymerase(s) is a DNA polymerase or a mixture of two or more different DNA polymerases.

9. The method of claim 5, wherein the microarray is a genomic DNA array.

10. The method of either of claim 1 or 5, wherein the modified nucleotides are labeled nucleotides that are fluorescent, enzymatic, chemiluminescent or radioactive, or nucleotides conjugated to a molecule that binds to a label which is fluorescent, enzymatic, chemiluminescent or radioactive.

* * * * *

UNITED STATES PATENT AND TRADEMARK OFFICE
CERTIFICATE OF CORRECTION

PATENT NO. : 7,141,371 B2 Page 1 of 1
APPLICATION NO. : 10/236598
DATED : November 28, 2006
INVENTOR(S) : Guowen Liu It is certified that error appears in the above-identified patent and that said Letters Patent is hereby corrected as shown below:

In the Specification:

In column 4, line 1, "(FIG. 2) In" should be --(FIG. 2). In--.

In column 4, line 59, "(µI)" should be --(µl)--.

In column 6, line 13, "1 µof" should be --1 µl of--.

In the Claims:

In Claim 5 (Col. 8, line 20), "c)" should be --e) --.

Signed and Sealed this

Twentieth Day of March, 2007

JON W. DUDAS
*Director of the United States Patent and Trademark Office*

UNITED STATES PATENT AND TRADEMARK OFFICE
CERTIFICATE OF CORRECTION

PATENT NO.       : 7,141,371 B2                                Page 1 of 1
APPLICATION NO.  : 10/236598
DATED            : November 28, 2006
INVENTOR(S)      : Guowen Liu It is certified that error appears in the above-identified patent and that said Letters Patent is hereby corrected as shown below:

In the Specification:

In column 4, line 1, "(FIG. 2) In" should be --(FIG. 2). In--.

In column 4, line 59, "(µI)" should be --(µl)--.

In column 5, line 60 "µI" should be -- µl --.

In column 6, line 13, "1 µof" should be --1 µl of--.

In the Claims:

In Claim 5 (Col. 8, line 20), "c)" should be --e) --.

This certificate supersedes Certificate of Correction issued March 20, 2007.

Signed and Sealed this

Twenty-second Day of May, 2007

JON W. DUDAS
*Director of the United States Patent and Trademark Office*